(12) United States Patent
Yoo et al.

(10) Patent No.: US 9,923,169 B2
(45) Date of Patent: Mar. 20, 2018

(54) ENCAPSULANT FILM (71) Applicant: LG CHEM, LTD., Seoul (KR)

(72) Inventors: Hyun Jee Yoo, Daejeon (KR); Seung Min Lee, Daejeon (KR); Yoon Gyung Cho, Daejeon (KR); Kyung Yul Bae, Daejeon (KR); Jung Sup Shim, Daejeon (KR); Suk Ky Chang, Daejeon (KR); Hyun Suk Kim, Daejeon (KR); Jung Ok Moon, Daejeon (KR); Ban Seok Choi, Daejeon (KR); Se Woo Yang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/899,518

(22) PCT Filed: Jun. 19, 2014

(86) PCT No.: PCT/KR2014/005451
§ 371 (c)(1),
(2) Date: Dec. 17, 2015

(87) PCT Pub. No.: WO2014/204257
PCT Pub. Date: Dec. 24, 2014

(65) Prior Publication Data
US 2016/0155987 A1  Jun. 2, 2016

(30) Foreign Application Priority Data

Jun. 19, 2013 (KR) .................. 10-2013-0070637
Jun. 19, 2014 (KR) .................. 10-2014-0075199

(51) Int. Cl.
*H01L 51/00* (2006.01)
*H01L 51/54* (2006.01)
*C08K 3/10* (2006.01)
*C08K 3/22* (2006.01)
*C08K 3/32* (2006.01)
*C08K 3/36* (2006.01)
*H01L 51/52* (2006.01)
*C08J 5/18* (2006.01)
*G01N 21/958* (2006.01)

(52) U.S. Cl.
CPC ............ *H01L 51/5259* (2013.01); *C08J 5/18* (2013.01); *G01N 21/958* (2013.01); *H01L 51/0034* (2013.01); *H01L 51/0043* (2013.01); *C08K 3/10* (2013.01); *C08K 3/22* (2013.01); *C08K 3/32* (2013.01); *C08K 3/36* (2013.01); *C08L 2203/206* (2013.01)

(58) Field of Classification Search
None
See application file for complete search history.

(56) References Cited

U.S. PATENT DOCUMENTS

| | | | |
|---|---|---|---|
| 8,405,233 B2 | 3/2013 | Blizzard et al. | |
| 8,771,459 B2 | 7/2014 | Keite et al. | |
| 2004/0191566 A1* | 9/2004 | Kikuchi | H01L 51/529 428/690 |
| 2007/0152212 A1* | 7/2007 | Cho | H01L 51/5256 257/40 |
| 2013/0251989 A1 | 9/2013 | Yoo et al. | |
| 2014/0319497 A1 | 10/2014 | Cho et al. | |
| 2015/0287940 A1 | 10/2015 | Yoo et al. | |

FOREIGN PATENT DOCUMENTS

| | | |
|---|---|---|
| CN | 1585807 A | 2/2005 |
| CN | 101137505 A | 3/2008 |
| CN | 1015833685 A | 11/2009 |
| CN | 102272946 | 12/2011 |
| EP | 0836936 | 8/1997 |
| EP | 2637229 A2 | 9/2013 |
| EP | 2644677 A2 | 10/2013 |
| EP | 3001476 A1 | 3/2016 |
| EP | 3012284 A1 | 4/2016 |
| EP | 3109913 A1 | 12/2016 |
| JP | 2004-335183 A | 11/2004 |
| JP | 2007-188708 A | 7/2007 |
| JP | 2010080308 A | 4/2010 |
| JP | 2013-502028 A | 1/2013 |
| KR | 100467242 | 7/2005 |
| KR | 100669751 | 1/2007 |
| KR | 100838073 | 6/2008 |
| KR | 1020110119673 | 11/2011 |
| KR | 1020120046704 | 5/2012 |
| KR | 102013005541 | 5/2013 |
| NO | 2011/016408 A1 | 2/2011 |
| NO | 2012/070871 A2 | 5/2012 |
| WO | 2010077425 | 7/2010 |
| WO | 2012-060621 A2 | 5/2012 |
| WO | 2013073902 | 5/2013 |

OTHER PUBLICATIONS

G. Szitasi et al., "Integrated Electrical and Optical Characterization of Large Area Thin Film Photovoltaic Materials", Photovoltaic Specialists Conference (PVSC), 2012 38th IEEE, pp. 00474-00477.

* cited by examiner

*Primary Examiner* — Ramsey E Zacharia
(74) *Attorney, Agent, or Firm* — Dentons US LLP (57) ABSTRACT

There are provided a film and an organic electronic device. The present application may provide a film that may be provided for an evaluation method in which reliability of an encapsulant film is simply and easily evaluated only by measuring a haze immediately before the encapsulant film is used, thereby a failure of a product is determined and reliability may be predicted.

15 Claims, 3 Drawing Sheets

ENCAPSULANT FILM

CROSS-REFERENCE

This application is a National Stage Application of International Application No. PCT/KR2014/005451, filed Jun. 19, 2014, and claims priority to and the benefit of Korean Patent Application No. 10-2014-0075199, filed on Jun. 19, 2014 and Korean Patent Application No. 10-2013-0070637, filed Jun. 19, 2013, the contents of each which is incorporated by reference in its entirety for all purposes as if fully set forth below.

TECHNICAL FIELD

The present application relates to an encapsulant film and an organic electronic device including the film.

BACKGROUND ART

Encapsulant films may be used for protecting elements, devices, and the like which are sensitive to external factors such as moisture or oxygen. The elements or devices that may be protected by the encapsulant film include, for example, organic electronic devices, solar cells, or rechargeable batteries such as lithium rechargeable batteries. In particular, among the elements or the devices, organic electronic devices are vulnerable to external factors such as water or oxygen.

The organic electronic device is a device including a functional organic material. As the organic electronic device or an organic electronic element included in the organic electronic device, a photovoltaic device, a rectifier, a transmitter, an organic light emitting diode (OLED), and the like may be exemplified.

In general, organic electronic devices are vulnerable to external factors such as water. For example, an organic light emitting element generally includes a layer made of a functional organic material that is present between a pair of electrodes including a metal or a metal oxide. When water penetrates from the outside, there are problems in which the layer made of the organic material is exfoliated due to an influence of moisture at an interface with the electrode, the electrode is oxidized by water which results in an increase in a resistance value, and the organic material itself is degenerated which results in a loss of a light-emitting function or a decrease in brightness.

Accordingly, in order to protect organic light emitting elements from elements of an external environment such as water, an encapsulation structure in which an organic light emitting element formed on a substrate is covered by a glass or metal can having a getter or a moisture absorbent provided therein and is fixed with an adhesive, and the like is used. Also, a method of sealing the organic light emitting element using an encapsulant film instead of the encapsulation structure is used.

DISCLOSURE

Technical Problem

The present application relates to a novel encapsulant film and an organic electronic device including the film.

Technical Solution

According to an aspect of the present application, there is provided an encapsulant film, and particularly, an encapsulant film for encapsulating an organic light emitting element of an organic electronic device. The encapsulant film of the present application includes a moisture absorbent to exhibit a haze reduction property caused by a reaction of the moisture absorbent with water. Therefore, reliability of the film may be evaluated by measuring the haze of the encapsulant film including the moisture absorbent. When an organic electronic device panel is manufactured, since it is possible to determine availability of the film simply by measuring the haze before the encapsulant film is used, it is possible to provide the film capable of minimizing a failure rate of the organic electronic device.

In an embodiment of the present application, the film may satisfy the following General Equation 1.

$$D = k/Hz \qquad \text{[General Equation 1]}$$

In General Equation 1, Hz represents a haze value (%) of the film that is measured within one hour from a time point at which the film is taken out of a water-resistant sealed envelope under conditions of a relative humidity of 50% at 25° C. using the haze meter, D represents a water penetration distance (mm) of the film that is measured after the film of which a haze is measured is laminated between two glass substrates and maintained under conditions of a temperature of 85° C. and a relative humidity of 85% for 0 to 1500 hours, and k represents a value equal to or greater than one as a proportionality constant.

In the above description, the water penetration distance represents a length or a distance to which water penetrates from an outermost edge of the film toward a center of the film after the film of which a haze is measured is laminated between two glass substrates and maintained under conditions of a temperature of 85° C. and a relative humidity of 85% for 0 to 1500 hours. For example, a ruler, a vernier caliper, an optical microscope, and the like may be used to measure the water penetration distance, but a measurement device is not limited thereto.

In an example, in the film according to the present application satisfying General Equation 1, a relation between the measured haze value of the film and the water penetration distance may be inversely proportional. For example, as the haze value of the film increases, the water penetration distance of the film may decrease. That is, when a higher haze value of the film according to the present application is measured, water does not easily penetrate into the film. Accordingly, evaluation of the reliable lifespan of the film, which will be described below, may be performed simply by measuring the haze.

In another embodiment of the present application, the film of the present application may satisfy the following General Equation 2.

$$D = -\alpha \times Hz + \beta \qquad \text{[General Equation 2]}$$

In General Equation 2, Hz represents a haze value (%) of the film that is measured within one hour from a time point at which the film is taken out of the water-resistant sealed envelope under conditions of a relative humidity of 50% at 25° C. using the haze meter, D represents a water penetration distance (mm) of the film that is measured after the film is laminated between two glass substrates and maintained under conditions of a temperature of 85° C. and a relative humidity of 85% for 0 to 1500 hours, α is 0.01 or more, and β is 1.0 or more and greater than D.

The film of the present application may satisfy a relation between the haze and the water penetration distance defined in General Equation 2. For example, measured values of the haze and the water penetration distance of the film of the present application may be present in an area in which a straight line of General Equation 2 may be drawn. Accordingly, as described above, it is possible to evaluate the reliable lifespan of the film simply by measuring the haze.

α represents a slope of a straight line represented by General Equation 2, and may be 0.01 or more, for example, 0.015 or more, 0.02 or more, 0.025 or more, 0.03 or more, 0.035 or more, 0.04 or more, or 0.045 or more, but the value is not limited thereto. The slope may increase as a time for which the film is exposed to water increases, when the water penetration distance of the film is measured. An upper limit of the slope is not specifically limited, but may be adjusted to a range in which an x axis representing the haze value and the straight line in General Equation 2 are not perpendicular, and may be, for example, 0.9 or less, 0.8 or less, 0.7 or less, 0.5 or less, 0.4 or less, 0.3 or less, 0.2 or less, or 0.1 or less.

β represents a y-intercept of the straight line representation of General Equation 2, and may be 1.0 or more, 2.0 or more, 3.0 or more, 4.0 or more, 5.0 or more, 6.0 or more, 7.0 or more, or 8.0 or more, but the value is not limited thereto. A value of the y-intercept may also increase as a time for which the film is exposed to water increases, when the water penetration distance of the film is measured. An upper limit of the y-intercept is not specifically limited, but may be 15 or less, 14 or less, 13 or less, 12 or less, 11 or less or 10 or less.

FIGS. 1 to 4 are graphs showing the relation between the water penetration distance and the haze which were measured after the films of the present application were maintained under conditions of a temperature of 85° C. and a relative humidity of 85% for 100 hours, 300 hours, 500 hours, and 1000 hours, respectively.

As shown in FIGS. 1 to 4, it may be seen that there is a constant relation between the haze and the water penetration distance. In particular, it may be seen that the water penetration distance decreases as the haze value increases. Also, it may be seen that the slope and the y-intercept in General Equation 2 increase when a time for which the film is exposed to a humidity condition increases.

In an exemplary film of the present application, conditions of General Equation 1 and/or General Equation 2 may be satisfied for the encapsulant film for encapsulating an organic electronic device having the same bezel size. For example, when a bezel size of the organic electronic device is fixed at any value in a range of 2 mm to 20 mm, the encapsulant film in the organic electronic device may satisfy General Equation 1 and/or General Equation 2.

Also, conditions of General Equation 1 and/or General Equation 2 may be satisfied in one film or two or more films including moisture absorbent having the same conditions, for example, the moisture absorbent of the same type, the same content and/or the same average particle diameter, but the present invention is not limited thereto.

The film of the present application satisfying General Equation 1 and/or General Equation 2 includes a base resin and moisture absorbent. For example, when the film of the present application including the base resin and moisture absorbent is left in wet conditions, the haze may decrease, and thereby General Equation 1 and/or 2 may be satisfied. That is, due to a hydration reaction of the moisture absorbent included in the film with water which has penetrated into the film, a hydrate, which is an aggregate of metal oxides, is generated from an outermost portion of the moisture absorbent, downsizing of an effective moisture absorbent aggregate that reacts with water results and thereby the haze may decrease. Also, due to a change in a refractive index of the moisture absorbent caused by the hydration reaction, the refractive index matches a refractive index of an organic binder and the haze decreases. Accordingly, in order to apply the encapsulant film being stored to the panel, it is necessary to ensure the number of effective particles of the moisture absorbent which may react with water to a predetermined level or more, which means that the haze needs to be maintained at a predetermined level or more.

In another embodiment of the present application, the haze of the encapsulant film may satisfy the following General Equation 3.

$$Hz \geq 30\% \qquad \text{[General Equation 3]}$$

In General Equation 3, Hz represents haze of the film measured by the haze meter. The haze value is not specifically limited, but may be a value measured with respect to, for example, a film having a thickness of 30 μm or 40 μm.

The haze may be 30% or more, for example, 40% or more or 50% or more. In order to suppress damage of the organic electronic element, the haze value of the film is adjusted to the above range according to a length of the bezel of the composing organic electronic device so that the lifespan of the organic electronic device is secured. In this case, since the moisture absorbent has a light scattering characteristic, it may be appropriately applied to an organic electronic device of a bottom emission type particularly.

Also, the haze may be a value measured from, for example, a film having a water penetration distance D of less than 10 mm. When the haze satisfies the above range with a water penetration distance of less than 10 mm, a correlation having high reliability between the haze and the water penetration distance of General Equation 1 and/or General Equation 2 may be derived.

In an example, the film may be a curable hot melt type adhesive film. The term "hot melt type adhesive film" used in this specification may refer to a film that maintains a solid or semi-solid state at room temperature, melts and exhibits adhesiveness when appropriate heat is applied, and is able to firmly fix an object material, as an adhesive after curing. Also, the term "curing of the adhesive" in this specification may refer to a chemical or physical action or reaction which enables the object material to be changed to exhibit an adhesive property. Also, the term "room temperature" refers to a natural temperature without any introduced heating or cooling, and may refer to a temperature of, for example, about 15° C. to 35° C., about 20° C. to 25° C., or about 25° C. or 23° C. Also, in the above description, maintaining the solid or semi-solid state at room temperature may refer to the fact that the object material exhibits a viscosity of about $10^6$ poise or more, or about $10^7$ poise or more at room temperature. In the above description, the viscosity is measured using an advanced rheometric expansion system (ARES). In the above description, an upper limit of the viscosity is not specifically limited, and may be, for example, about $10^9$ poise or less.

For example, when contained components are not cured, the film may maintain a solid or semi-solid state at room temperature. That is, a curable resin composition may be included in the form of a film. Therefore, it is possible to provide a film that is easy to handle, prevents physical or chemical damage of elements in application of an encapsulation process and the like, and can be smoothly processed.

In an example, a water vapor transmission rate (WVTR) of the film may be 50 g/m²-day or less or 30 g/m²-day or less. The WVTR may be a WVTR measured with respect to a film having a thickness of 100 wn under a relative humidity of 100% at 100° C. in a thickness direction of the film. The WVTR of the film is controlled as described above so that a film exhibiting an excellent water barrier property may be provided. A lower WVTR may indicate a more excellent water barrier property, and a lower limit thereof is not specifically limited. A lower limit of the WVTR of the film may be, for example, 0 g/m²-day.

In the embodiments of the present application, as the base resin included in the encapsulant film, a thermoplastic resin or an elastomer may be used, or a curable resin may be used without limitation.

In an example, examples of the thermoplastic resin or the elastomer, and the curable resin may include a styrene-based resin or elastomer, a polyolefin-based resin or elastomer, a polyoxyalkylene-based resin or elastomer, a polyester-based resin or elastomer, a polyvinyl-chloride-based resin or elastomer, a polycarbonate-based resin or elastomer, a polyphenylene-sulfide-based resin or elastomer, mixtures of hydrocarbons, a polyamide-based resin or elastomer, an acrylate-based resin or elastomer, an epoxy-based resin, a silicone-based resin or elastomer, a fluorine-based resin or elastomer, other elastomers, or mixtures thereof.

In the above description, examples of the styrene-based resin or elastomer may include a styrene-ethylene-butadiene-styrene block copolymer (SEBS), a styrene-isoprene-styrene block copolymer (SIS), an acrylonitrile-butadiene-styrene block copolymer (ABS), an acrylonitrile-styrene-acrylate block copolymer (ASA), a styrene-butadiene-styrene block copolymer (SBS), a styrene-based homopolymer, or mixtures thereof. Examples of the olefin-based resin or elastomer may include a high-density polyethylene-based resin or elastomer, a low-density polyethylene-based resin or elastomer, a polypropylene-based resin or elastomer, or mixtures thereof. Examples of the elastomer may include an ester-based thermoplastic elastomer, an olefin-based elastomer, a silicone-based elastomer, an acrylic-based elastomer, or mixtures thereof. Among these, as the olefin-based thermoplastic elastomer, a polybutadiene resin or elastomer, a polyisobutylene resin or elastomer, and the like may be used. Examples of the polyoxyalkylene-based resin or elastomer may include a polyoxymethylene-based resin or elastomer, a polyoxyethylene-based resin or elastomer, or mixtures thereof. Examples of the polyester-based resin or elastomer may include a polyethylene-terephthalate-based resin or elastomer, a polybutylene-terephthalate-based resin or elastomer, or mixtures thereof. Examples of the polyvinyl chloride-based resin or elastomer may include polyvinylidene chloride and the like. Examples of the mixtures of hydrocarbons may include hexatriacotane, paraffin, and the like. Examples of the polyamide-based resin or elastomer may include nylon and the like. Examples of the acrylate-based resin or elastomer may include polybutyl(meth)acrylate and the like. Examples of the epoxy-based resin may include a bisphenol type such as a bisphenol A type, a bisphenol F type, a bisphenol S type and water-added materials thereof; a novolac type such as a phenol novolac type and a cresol novolac type; a nitrogen-containing ring type such as a triglycidyl isocyanurate type and a hydantoin type; an alicyclic type; an aliphatic type; a naphthalene type, an aromatic type such as a biphenyl type; a glycidyl type such as a glycidyl ether type, a glycidylamine type, and a glycidyl ester type; a dicyclo type such as a dicyclopentadiene type; an ester type; an etherester type, or mixtures thereof. Examples of the silicone-based resin or elastomer may include polydimethylsiloxane and the like. Also, examples of the fluorine-based resin or elastomer may include a polytrifluoroethylene resin or elastomer, a polytetrafluoroethylene resin or elastomer, a polychlorotrifluoroethylene resin or elastomer, a polyhexafluoropropylene resin or elastomer, polyvinylidene fluoride, polyvinyl fluoride, poly(fluorinated ethylene-propylene), or mixtures thereof.

When the listed resins or elastomers are used, they may be grafted with, for example, maleic anhydride and the like, may be copolymerized with other listed resins or elastomers, or monomers for preparing resins or elastomers, or may be denaturalized by other compounds. Examples of the other compounds may include a carboxyl-terminated butadiene-acrylonitrile copolymer and the like In an embodiment of the present application, the base resin may be a thermoplastic elastomer or a thermoplastic resin.

Examples of the thermoplastic resin or elastomer may include a styrene-based resin or elastomer, a polyolefin-based resin or elastomer, other elastomers, a polyoxyalkylene-based resin or elastomer, a polyester-based resin or elastomer, a polyvinyl-chloride-based resin or elastomer, a polycarbonate-based resin or elastomer, a polyphenylene-sulfide-based resin or elastomer, mixtures of hydrocarbons, a polyamide-based resin or elastomer, an acrylate-based resin or elastomer, a silicone-based resin or elastomer, a fluorine-based resin or elastomer, or mixtures thereof.

In an example, the thermoplastic resin may be a copolymer of olefin-based compounds having a carbon-carbon double bond, but the resin is not limited thereto. Also, the base resin may be a copolymer of diene and an olefin-based compound having a single carbon-carbon double bond. Here, the olefin-based compound may include isobutylene, propylene, ethylene, and the like. The diene may be a monomer that may be polymerized with the olefin-based compound, and may include, for example, 1-butene, 2-butene, isoprene, or butadiene. That is, as the base resin, for example, a homopolymer of an isobutylene monomer; a copolymer obtained by copolymerizing the isobutylene monomer with other polymerizable monomers; or mixtures thereof may be used. In an example, the copolymer of the olefin-based compound having a single carbon-carbon double bond and the diene may be butyl rubber.

The thermoplastic elastomer base resin may have a weight-average molecular weight (Mw) at which molding in the form of a film is possible. For example, the resin may have a weight-average molecular weight of about 100,000 to 2,000,000, 100,000 to 1,500,000, or 100,000 to 1,000,000. The term "weight-average molecular weight" in this specification refers to a conversion value with respect to a standard polystyrene measured using gel permeation chromatography (GPC). However, the thermoplastic resin or elastomer component does not necessarily have the above-mentioned weight-average molecular weight. For example, when a molecular weight of the thermoplastic resin or elastomer component does not reach a level at which the film can be formed, a separate binder resin may be mixed as a component forming the encapsulant film.

In another embodiment, the base resin may be a curable resin. A detailed type of the curable resin that may be used in the present application is not specifically limited. For example, various thermosetting or photocurable resins known in the related art may be used. In the above description, the term "thermosetting resin" refers to a resin that may be cured by applying appropriate heat or an aging process, and the term "photocurable resin" refers to a resin that may be cured by irradiation of electromagnetic waves. Also, in the above description, a category of the electromagnetic waves may include microwaves, infrared (IR), ultraviolet (UV), X-rays, and γ-rays, and further include particle beams such as an α-particle beam, a proton beam, a neutron beam, and an electron beam. In the present application, an example of a photocurable type resin may include a cationic photocurable type resin. The term "cationic photocurable type resin" refers to a resin that may be cured by a cationic polymerization or cationic curing reaction derived by irradiation of electromagnetic waves. Also, the curable resin may be a dual curable type resin having thermosetting and photocurable properties.

As the curable resin, for example, as a resin that may exhibit an adhesive property by curing, a resin having at least one functional group or part that may be cured by heat such as a glycidyl group, an isocyanate group, a hydroxyl group, a carboxyl group, or an amide group may be used, and a resin having at least one functional group or part that may be cured by irradiation of active energy rays such as an epoxide group, a cyclic ether group, a sulfide group, an acetal group, or a lactone group may be used. Examples of the curable resin may include a polyolefin resin, an acryl resin, a polyester resin, an isocyanate resin, or an epoxy resin which has at least one functional group or part described above, but the curable resin is not limited thereto.

In an example, as the curable resin, an epoxy resin may be used. The epoxy resin may be an aromatic-based or aliphatic-based epoxy resin. As the epoxy resin, a thermosetting epoxy resin may be used or an active energy ray curable resin, for example, an epoxy resin that is cured by a cationic polymerization reaction due to irradiation of active energy rays, may be used.

The epoxy resin according to the example may have an epoxide equivalent weight of 150 g/eq to 2,000 g/eq. At epoxide equivalent weights within this range, properties of a cured product such as adhesive performance or a glass transition temperature may be maintained in an appropriate range. Examples of the epoxy resin may include a cresol novolac epoxy resin, a bisphenol A type epoxy resin, a bisphenol A type novolac epoxy resin, a phenol novolac epoxy resin, a tetrafunctional epoxy resin, a biphenyl type epoxy resin, a triphenylmethane type epoxy resin, an alkyl-modified triphenylmethane type epoxy resin, a naphthalene type epoxy resin, a dicyclopentadiene type epoxy resin, or a dicyclopentadiene-modified phenol type epoxy resin, and mixtures of thereof.

In the present application, an epoxy resin having a cyclic structure in its molecular structure may be preferably used. In an example, the epoxy resin may be an aromatic-based epoxy resin. The term "aromatic-based epoxy resin" in this specification may refer to an epoxy resin having at least one of an aromatic core such as a phenylene structure or an aromatic group such as a phenyl group at a main chain or side chain of the resin. When the aromatic-based epoxy resin is used, the cured product has excellent thermal and chemical stability and a low moisture permeation degree so that reliability of an electronic device encapsulation structure may increase. Examples of the aromatic-based epoxy resin may include a biphenyl type epoxy resin, a naphthalene type epoxy resin, a dicyclopentadiene type epoxy resin, a dicyclopentadiene-modified phenol type epoxy resin, a cresol-based epoxy resin, a bisphenol-based epoxy resin, a xylok-based epoxy resin, a multifunctional epoxy resin, a phenol novolac epoxy resin, a triphenolmethane type epoxy resin, an alkyl-modified triphenolmethane epoxy resin, or mixtures thereof, but the aromatic-based epoxy resin is not limited thereto.

In an example, the epoxy resin may be a silane-modified epoxy resin. As the silane-modified epoxy resin, for example, a product of a reaction of a silane compound and at least one epoxy resin among the above-described epoxy resins may be used. In this manner, when an epoxy resin that has been modified by silane and structurally has a silane group is used, an adhesive property with a glass substrate, a substrate inorganic material, and the like of the organic electronic device may be maximized, and a water barrier property, durability, reliability, and the like may increase. A detailed type of the epoxy resin that may be used in the present application is not specifically limited. Such a resin may be easily obtained from a supplier, for example, Kukdo Chemical Co., Ltd.

In the above description, as the silane compound, for example, a compound represented by the following Chemical Formula 1 may be exemplified.

[Chemical Formula 1]

In Chemical Formula 1, D represents an a vinyl group, an epoxy group, an amino group, an acryl group, a methacrylic group, a mercapto group, an alkoxy group, or an isocyanate group, or an alkyl group substituted with any functional group among these, Q represents hydrogen, an alkyl group, a halogen, an alkoxy group, an aryl group, an aryloxy group, an acyloxy group, an alkylthio group, or an alkyleneoxythio group, and n is 1 to 3.

As a compound with Chemical Formula 1, the functional group D may react with a functional group included in the epoxy resin and form the silane-modified epoxy resin.

When the functional group is, for example, the amino group, the amino group may react with an epoxy group of the epoxy resin, form a bond of "—CH(OH)—CH$_2$—NH—," and the silane compound may be introduced into the epoxy group.

Also, when the functional group D is the isocyanate group or the alkoxy group, the silane compound may be introduced by reacting with an epoxy resin containing a hydroxyl group (OH), for example, a bisphenol type epoxy resin such as a bisphenol F type epoxy resin, a bisphenol F type novolac epoxy resin, a bisphenol A type epoxy resin, or a bisphenol A type novolac epoxy resin.

In Chemical Formula 1, as the alkyl group, an alkyl group having 1 to 20 carbon atoms, 1 to 16 carbon atoms, 1 to 12 carbon atoms, 1 to 8 carbon atoms, or 1 to 4 carbon atoms may be exemplified. The alkyl group may be a straight chain, branched, or a cyclic type alkyl group.

In Chemical Formula 1, as a halogen atom, fluorine (F), chlorine (Cl), bromine (Br), iodine (I), and the like may be exemplified.

Also, in Chemical Formula 1, as the alkoxy group, an alkoxy group having 1 to 20 carbon atoms, 1 to 12 carbon atoms, 1 to 8 carbon atoms, or 1 to 4 carbon atoms may be exemplified. The alkoxy group may be a straight chain, branched, or a cyclic type.

Also, in Chemical Formula 1, as the aryl group or as the aryl group included in the aryloxy group, in addition to the aryl group, an aralkyl group and the like may be included. For example, the aryl group may refer to a compound having at least one benzene ring or a structure in which two or more benzene rings are connected or condensed or a monovalent residue derived from a derivative thereof. The aryl group may be, for example, an aryl group having 6 to 25 carbon atoms, 6 to 21 carbon atoms, 6 to 18 carbon atoms, or 6 to 12 carbon atoms. Examples of the aryl group may include a phenyl group, a dichlorophenyl group, a chlorophenyl group, a phenylethyl group, a phenylpropyl group, a benzyl group, a tolyl group, a xylyl group, or a naphthyl group.

Also, in Chemical Formula 1, as the acyloxy group, an acyloxy group having 1 to 20 carbon atoms, 1 to 16 carbon atoms, or 1 to 12 carbon atoms may be exemplified.

Also, in Chemical Formula 1, as the alkylthio group, an alkylthio group having 1 to 20 carbon atoms, 1 to 16 carbon atoms, 1 to 12 carbon atoms, 1 to 8 carbon atoms, or 1 to 4 carbon atoms may be exemplified. As the alkyleneoxythio group, an alkyleneoxythio group having 1 to 20 carbon atoms, 1 to 16 carbon atoms, 1 to 12 carbon atoms, 1 to 8 carbon atoms, or 1 to 4 carbon atoms may be exemplified.

The alkyl group, the alkoxy group, the aryl group, the acyloxy group, the alkylthio group, or the alkyleneoxythio group may be arbitrarily substituted with at least one substituent. Examples of the substituent may include a hydroxyl group, an epoxy group, an alkyl group, an alkenyl group, an alkynyl group, an alkoxy group, an acyl group, a thiol group, an acryloyl group, a methacryloyl group, an aryl group, or an isocyanate group, but the substituent is not limited thereto.

In Chemical Formula 1, the functional group D may be, for example, the alkoxy group, the amino group, or the isocyanate group among them.

Also, in Chemical Formula 1, at least one, two or more, or three of the functional group Q may be, for example, a halogen atom, the alkoxy group, the aryloxy group, the acyloxy group, the alkylthio group, the alkyleneoxythio group, or the alkoxy group.

As the silane-modified epoxy resin, for example, an epoxy resin in which a silane compound of about 0.1 parts by weight to about 10 parts by weight, about 0.1 parts by weight to about 9 parts by weight, about 0.1 parts by weight to about 8 parts by weight, about 0.1 parts by weight to about 7 parts by weight, about 0.1 parts by weight to about 6 parts by weight, about 0.1 parts by weight to about 5 parts by weight, about 0.1 parts by weight to about 4 parts by weight, about 0.1 parts by weight to about 3 parts by weight, about 0.3 parts by weight to 2 parts by weight, or about 0.5 parts by weight to about 2 parts by weight is introduced with respect to 100 parts by weight of the epoxy resin may be used. In an example, the epoxy resin into which the silane compound is introduced may be the aromatic-based epoxy resin. Examples of the aromatic-based epoxy resin may a bisphenol type epoxy resin such as a bisphenol F type epoxy resin, a bisphenol F type novolac epoxy resin, a bisphenol A type epoxy resin, or a bisphenol A type novolac epoxy resin.

When the base resin is the curable resin, the encapsulant film may additionally include an epoxy curable binder resin. When a curing base resin is molded in the form of a film or a sheet, the epoxy curable binder resin may improve moldability.

A type of the epoxy curable binder resin is not specifically limited, as long as it has compatibility with other resins such as a curable resin. As the epoxy curable binder resin, a phenoxy resin, an acrylate resin, or a high molecular weight epoxy resin may be used. In the above description, the high molecular weight epoxy resin may refer to, for example, a resin having a weight-average molecular weight of about 2,000 to 6,000. As the high molecular weight epoxy resin, a solid type bisphenol A type epoxy resin, a solid type bisphenol F type epoxy resin, and the like may be exemplified. As the epoxy curable binder resin, a rubber component such as a high polarity functional group-containing rubber or high polarity functional group-containing reactive rubber may be used. In an example, as the epoxy curable binder resin, the phenoxy resin may be used.

In embodiments of the present application, the encapsulant film encapsulating the organic electronic element may have a multi-layer structure including a first layer that comes in contact with the organic electronic device and a second layer that does not come in contact with the organic electronic device when the encapsulant film encapsulates the organic electronic device. Here, the multi-layer structure does not necessarily mean a two-layer structure but may include a structure having two or more layers depending on characteristics required for manufacturing the panel.

Depending on characteristics and economic feasibility of the panel, both of the first layer and the second layer may be made of a curing base resin or a thermoplastic elastomer base resin. Also, the multi-layer structure may be formed by mixing a layer made of the curing base resin and a layer made of the thermoplastic elastomer base resin. In an example, the first layer and second layer may include any one resin of the polyolefin-based resin and the epoxy-based resin. For example, the multi-layer structure may include a structure in which the first layer is made of the polyolefin-based resin and the second layer is made of the epoxy-based resin; a structure in which both of the first layer and the second layer are made of the polyolefin-based resin; a structure in which the first layer is made of the epoxy-based resin and the second layer is made of the polyolefin-based resin; and a structure in which both of the first layer and the second layer are made of the epoxy-based resin.

In embodiments of the present application, the encapsulant film includes the moisture absorbent. The term "moisture absorbent" in this specification may refer to, for example, a material that may absorb water by a chemical reaction with water or moisture that has penetrated into the encapsulant film.

In an example, the moisture absorbent may include a water reactive adsorbent, a physical adsorbent, or mixtures thereof. The water reactive adsorbent may absorb water or moisture by chemically reacting with moisture, water, oxygen, and the like introduced into the encapsulant film. The physical adsorbent may suppress penetration of water or moisture by making a flow path of water or moisture penetrating into an encapsulation structure longer, and may maximize a barrier property against water and moisture through a matrix structure of the base resin and an interaction with the water reactive adsorbent, and the like.

A detailed type of the moisture absorbent that may be used in the present application is not specifically limited. The water reactive adsorbent may include, for example, a metal powder such as alumina, a metal oxide, a metal salt, phosphorus pentoxide ($P_2O_5$), or a mixture thereof. The physical adsorbent may include silica, zeolite, titania, zirconia, montmorillonite, and the like.

In the above description, specific examples of the metal oxide may include phosphorus pentoxide ($P_2O_5$), lithium oxide ($Li_2O$), sodium oxide ($Na_2O$), barium oxide (BaO), calcium oxide (CaO), or magnesium oxide (MgO). Examples of the metal salt may include sulfates such as lithium sulfate ($Li_2SO_4$), sodium sulfate ($Na_2SO_4$), calcium sulfate ($CaSO_4$), magnesium sulfate ($MgSO_4$), cobalt sulfate ($CoSO_4$), gallium sulfate ($Ga_2(SO_4)_3$), titanium sulfate ($Ti(SO_4)_2$) or nickel sulfate ($NiSO_4$), metal halides such as calcium chloride ($CaCl_2$), magnesium chloride ($MgCl_2$), strontium chloride ($SrCl_2$), yttrium chloride ($YCl_3$), copper chloride ($CuCl_2$), cesium fluoride (CsF), tantalum fluoride ($TaF_5$), niobium fluoride ($NbF_5$), lithium bromide (LiBr), calcium bromide ($CaBr_2$), cesium bromide ($CeBr_3$), selenium bromide ($SeBr_4$), vanadium bromide ($VBr_3$), magnesium bromide ($MgBr_2$), barium iodide ($BaI_2$) or magnesium iodide ($MgI_2$), metal chlorates such as barium perchlorate ($Ba(ClO_4)_2$) or magnesium perchlorate ($Mg(ClO_4)_2$), and the like, but the metal salt is not limited thereto.

In the present application, the moisture absorbent, such as the metal oxide, may be appropriately processed and mixed with the composition. For example, according to a type of the organic electronic device to which the encapsulant film may be applied, the encapsulant film may be a thin film having a thickness of 30 μm or less. In this case, a grinding process of the moisture absorbent may be necessary. In order to grind the moisture absorbent, a process such as three-roll milling, bead milling, ball milling, and the like may be used. Also, when the encapsulant film of the present application is used in a top emission type organic electronic device, and the like, transmittance of the encapsulant film itself is very important, and thereby a size of the moisture absorbent needs to be reduced. Therefore, the grinding process may be necessary for such a purpose.

The encapsulant film of the present application may include the moisture absorbent of 1 part by weight to 200 parts by weight, and preferably, 5 parts by weight to 100 parts by weight, with respect to 100 parts by weight of the base resin. By controlling the moisture absorbent to have a content of 5 parts by weight or more, the encapsulant film may exhibit an excellent water and moisture barrier property. In addition, by controlling the moisture absorbent to have a content of 100 parts by weight or less, the encapsulation structure of the thin film may be formed and the excellent water barrier property may be exhibited. Unless otherwise defined in this specification, the unit "parts by weight" refers to a weight ratio between components.

In an embodiment, when the encapsulant film of the present application is a multi-layer film including a first layer that comes in contact with the organic electronic element and a second layer that does not come in contact with the organic electronic device, the first layer may include 0 to 20% of the moisture absorbent with respect to a mass of the total moisture absorbent in the film, and the second layer may include 80 to 100% of the moisture absorbent with respect to a mass of the total moisture absorbent in the film.

That is, with respect to the mass of the total moisture absorbent in the encapsulant film, 0 to 20%, 0 to 18%, 0 to 16%, 0 to 14%, 0 to 12%, 0 to 10%, 0 to 8%, 0 to 6%, 0 to 4%, or 0 to 2% of the moisture absorbent may be included in the first layer. Also, 80 to 100%, 82 to 100%, 84 to 100%, 86 to 100%, 88 to 100%, 90 to 100%, 92 to 100%, 94 to 100%, 96 to 100%, or 98 to 100% of the moisture absorbent may be included in the second layer. When a content of the moisture absorbent in the first layer that is closer to the organic electronic device exceeds 20%, the moisture absorbent may press the organic electronic device together with a foreign material and cause physical damage, and a large amount of ionic materials may be discharged after reacting with water and cause chemical damage to a cathode or an inorganic protective film.

Also, in an example, when the encapsulant film of the present application has a multi-layer structure, the first layer may include the moisture absorbent at 0 parts by weight to 10 parts by weight, with respect to 100 parts by weight of the base resin. When the moisture absorbent is included at 0 parts by weight, the first layer has no moisture absorbent and only the second layer has the moisture absorbent. By controlling the moisture absorbent to have a content of 10 parts by weight or less with respect to 100 parts by weight of the base resin, the water barrier property may be maximized and the physical and chemical damage of the organic electronic device due to the moisture absorbent may be minimized.

In an example, the moisture absorbent may be in a uniformly dispersed state in the base resin or in the film. Here, the uniformly dispersed state may refer to a state in which the moisture absorbent has the same density or substantially the same density in any part of the base resin or a matrix of the film. The moisture absorbent may be controlled to have an appropriate size depending on usage purposes of the film. In an example, the moisture absorbent may be controlled to have an average particle diameter of 100 to 15000 nm. The moisture absorbent having a size in the above range is easy to store since a reaction rate with water is not too fast, an element to be encapsulated is not harmed, and water may be effectively removed.

In detailed embodiments of the present application, the encapsulant film may further include a tackifier according to a type of the base resin. For example, when the above-described base resin is the thermoplastic elastomer base resin, the encapsulant film may further include the tackifier. As the tackifier, for example, a hydrogenated petroleum resin obtained by hydrogenating a petroleum resin may be used. The hydrogenated petroleum resin may be partially or entirely hydrogenated, or may be a mixture thereof. As the tackifier, a tackifier having good compatibility with components constituting the encapsulant film and an excellent water barrier property may be selected. Specific examples of the hydrogenated petroleum resin may include a hydrogenated terpene-based resin, a hydrogenated ester-based resin, a hydrogenated dicyclopentadiene-based resin, and the like. The tackifier may have a weight-average molecular weight of about 200 to 5,000. A content of the tackifier may be appropriately adjusted as necessary. For example, the tackifier may be included in a ratio of 5 parts by weight to 100 parts by weight with respect to 100 parts by weight of the base resin.

In addition to the above-described components, various additives may be included in the encapsulant film according to a usage of the film and a manufacturing process of the film. For example, when the base resin is the thermoplastic elastomer base resin, a crosslinking material may be further included in the encapsulant film in consideration of durability and processability. Here, the crosslinking material may refer to a material having a thermally cross-linkable functional group and/or active energy ray cross-linkable functional group that is separately included in addition to the components constituting the encapsulant film. Also, a content of the crosslinking material included in the encapsulant film may be adjusted according to a desired physical property of the film.

In a specific example of the present application, the encapsulant film may further include a curing agent according to a type of the base resin. For example, a curing agent that may form a crosslinking structure and the like by reacting with the above-described base resin, or an initiator that may initiate a curing reaction of the resin may be further included.

A type of the curing agent may be appropriately selected and used according to the base resin or a type of the functional group included in the resin.

In an example, when the base resin is the epoxy resin, curing agents of the epoxy resin known in the related art, for example, an amine curing agent, an imidazole curing agent, a phenol curing agent, a phosphorus curing agent, an anhydride curing agent, or mixtures thereof may be used as the curing agent, but the curing agent is not limited thereto.

In an example, as the curing agent, an imidazole compound that is in a solid state at room temperature and has a melting point or decomposition temperature of 80° C. or more may be used. Examples of such a compound may include 2-methylimidazole, 2-heptadecylimidazole, 2-phenylimidazole, 2-phenyl-4-methylimidazole, or 1-cyanoethyl-2-phenylimidazole, but the compound is not limited thereto.

A content of the curing agent may be selected according to a configuration of the composition, for example, a type or a ratio of the base resin. For example, the curing agent may be included in an amount of 1 part by weight to 20 parts by weight, 1 part by weight to 10 parts by weight or 1 part by weight to 5 parts by weight with respect to 100 parts by weight of the base resin. However, the weight ratio may be changed according to the base resin, a type and a ratio of the functional group of the resin, a crosslinking density to be implemented, and the like.

When the base resin is a resin that may be cured by irradiation of active energy rays, as the initiator, for example, a cationic photopolymerization initiator may be used.

As the cationic photopolymerization initiator, an onium-salt-based or organometallic-salt-based ionized cationic initiator, an organic-silane-based or latent-sulfonic-acid-based initiator or a nonionized cationic photopolymerization initiator may be used. As the onium-salt-based initiator, a diaryliodonium salt, a triarylsulfonium salt, an aryldiazonium salt, and the like may be exemplified. As the organometallic-salt-based initiator, an iron arene and the like may be exemplified. As the organic-silane-based initiator, an o-nitrobenzyl triaryl silyl ether, a triaryl silyl peroxide, an acyl silane, and the like may be exemplified. As the latent-sulfonic-acid-based initiator, an α-sulfonyloxy ketone, an α-hydroxymethyl benzoin sulfonate, and the like may be exemplified, but the initiator is not limited thereto.

In an example, as the cationic initiator, the ionized cationic photopolymerization initiator may be used.

Also, when the base resin is a resin that may be cured by irradiation of active energy rays, as the initiator, for example, a radical initiator may be used.

The radical initiator may be a photoinitiator or a thermal initiator. A specific type of the photoinitiator may be appropriately selected in consideration of a cure rate, possibility of yellowing, and the like. For example, a benzoin-based, hydroxy-ketone-based, amino-ketone-based, or phosphine-oxide-based photoinitiator may be used. Specifically, benzoin, benzoin methyl ether, benzoin ethyl ether, benzoin isopropyl ether, benzoin n-butyl ether, benzoin isobutyl ether, acetophenone, dimethylamino acetophenone, 2,2-dimethoxy-2-phenyl-acetophenone, 2,2-diethoxy-2-phenylacetophenone, 2-hydroxy-2-methyl-1-phenylpropan-1-one, 1-hydroxycyclohexylphenylketone, 2-methyl-1-[4-(methylthio)phenyl]-2-morpholino-propan-1-one, 4-(2-hydroxyethoxy)phenyl-2-(hydroxy-2-propyl)ketone, benzophenone, p-phenyl benzophenone, 4,4'-diethylamino-benzophenone, dichlorobenzophenone, 2-methylanthraquinone, 2-ethylanthraquinone, 2-t-butylanthraquinone, 2-amino anthraquinone, 2-methylthioxanthone, 2-ethylthioxanthone, 2-chlorothioxanthone, 2,4-dimethylthioxanthone, 2,4-diethylthioxanthone, benzyldimethylketal, acetophenonedimethylketal, p-dimethylaminobenzoateester, oligo[2-hydroxy-2-methyl-1-[4-(1-methylvinyl)phenyl]propanone], 2,4,6-trimethylbenzoyl-diphenyl-phosphine oxide, and the like may be used.

A content of the initiator may be changed according to the base resin, a type and a ratio of the functional group of the resin, a crosslinking density to be implemented, and the like, as in the curing agent. For example, the initiator may be mixed in a ratio of 0.01 parts by weight to 10 parts by weight or 0.1 parts by weight to 3 parts by weight with respect to 100 parts by weight of the base resin.

In addition to the above-described components, various materials may be included in the encapsulant film according to a usage of the film and a manufacturing process of the film. For example, when the encapsulant film is molded in the form of a film or a sheet, the binder resin may be included in consideration of moldability, and the like.

In a specific example of the present application, the encapsulant film may include a filler, preferably an inorganic filler. The filler may suppress penetration of water or moisture by making moving path of water or moisture penetrating into an encapsulation structure longer, and may maximize a barrier property against water and moisture by an interaction with the base resin, the moisture absorbent, and the like. A detailed type of the filler that may be used in the present application is not specifically limited. For example, clay, talc, acicular silica, and mixtures thereof may be used.

Also, in the present application, in order to increase efficiency of binding with the filler and the organic binder, a product of which a surface is treated with an organic material may be used as the filler, or a coupling agent may be additionally added thereto.

The encapsulant film of the present application may include a filler in an amount of 1 part by weight to 50 parts by weight, and preferably 1 part by weight to 20 parts by weight with respect to 100 parts by weight of the base resin. By controlling a content of the filler to be 1 part by weight or more, it is possible to provide a cured product having an excellent water or moisture barrier property and mechanical property. Also, in the present application, by controlling a content of the filler to be 20 parts by weight or less, it is possible to manufacture a type of a film that provides an encapsulation structure exhibiting an excellent water barrier property, even when the encapsulant film is formed as a thin film.

In an embodiment of the present application, the film may satisfy the following General Equation 4.

$$Hz = -me^{-\varphi hr(n_g/n-1)^2}$$ [General Equation 4]

In General Equation 4, Hz represents a haze value (%) of the film that is measured within one hour from a time point at which the film is taken out of the water-resistant sealed envelope under conditions of a relative humidity of 50% at 25° C. using the haze meter, m represents a value greater than 0, Φ represents a content of the moisture absorbent with respect to the base resin, h represents a thickness of the film, r represents an average particle diameter of the moisture absorbent, $n_g$ represents a refractive index of the moisture absorbent, and n represents a refractive index of the base resin.

For example, the haze value of the film may be a value that is changed by the content of the moisture absorbent, the thickness of the film, the average particle diameter of the moisture absorbent, the refractive index of the moisture absorbent, and the refractive index of the base resin, which may satisfy the above relation. Therefore, when reliability of the film is evaluated by measuring the haze of the encapsulant film using a haze reduction property caused by a reaction of the moisture absorbent of the film with water, it is possible to evaluate reliability according to the absolute value of the haze and also evaluate reliability according to various haze values in consideration of the above parameters. For example, a haze of 10 is not unconditionally evaluated as having a shorter reliable lifespan than a haze of 20. Since evaluation may be performed in consideration of the parameters in General Equation 4, it is possible to evaluate the reliable lifespan more accurately.

Figure 1:
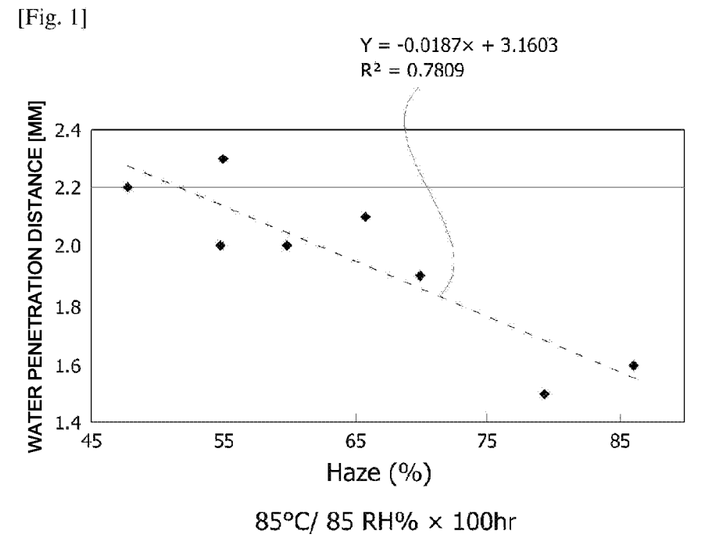
FIG. 1 is a graph showing a relation between a haze and a water penetration distance which are measured after a test specimen made of a film of the present application is maintained under conditions of a temperature of 85° C. and a relative humidity of 85% for 100 hours.
Figure 2:
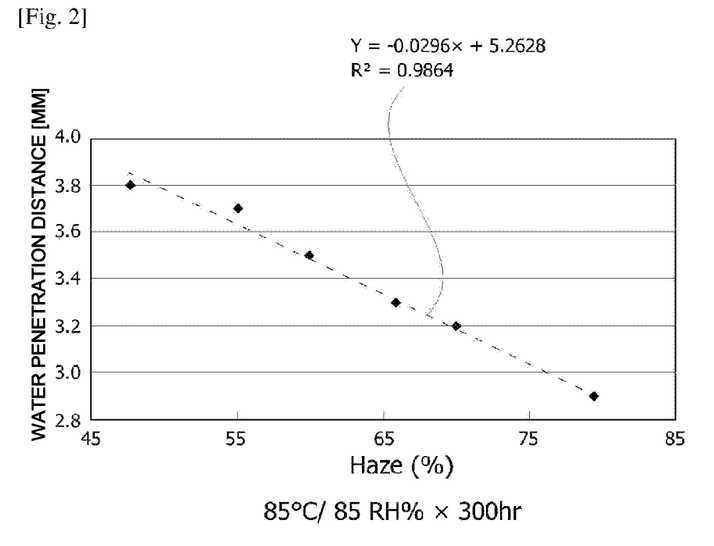
FIG. 2 is a graph showing a relation between a haze and a water penetration distance which are measured after a test specimen made using a film of the present application is maintained under conditions of a temperature of 85° C. and a relative humidity of 85% for 300 hours.
Figure 3:
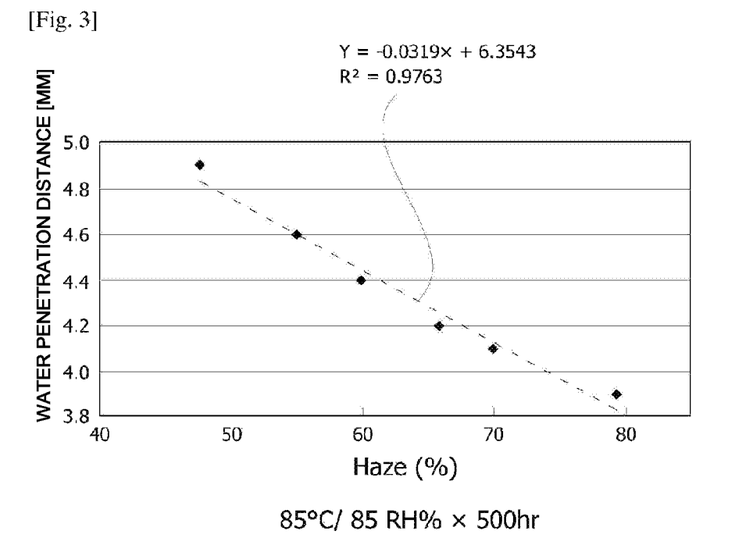
FIG. 3 is a graph showing a relation between a haze and a water penetration distance which are measured after a test specimen made using a film of the present application is maintained under conditions of a temperature of 85° C. and a relative humidity of 85% for 500 hours.
Figure 4:
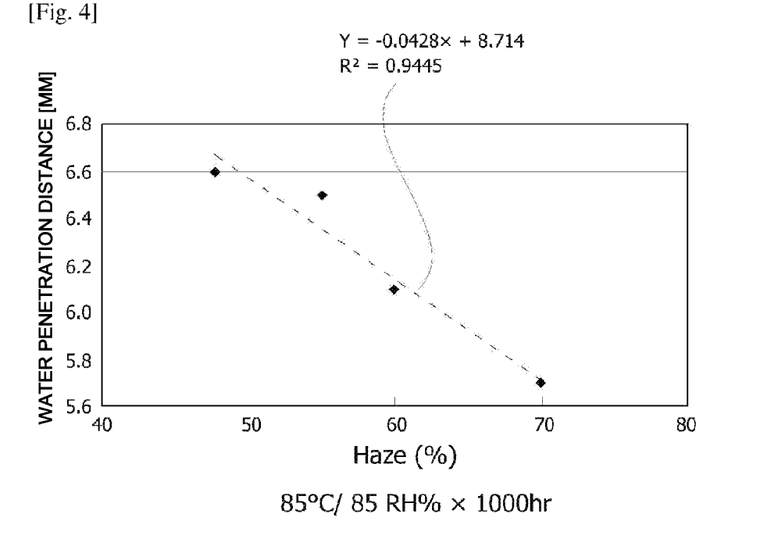
FIG. 4 is a graph showing a relation between a haze and a water penetration distance which are measured after a test specimen made using a film of the present application is maintained under conditions of a temperature of 85° C. and a relative humidity of 85% for 1000 hours.
Figure 5:
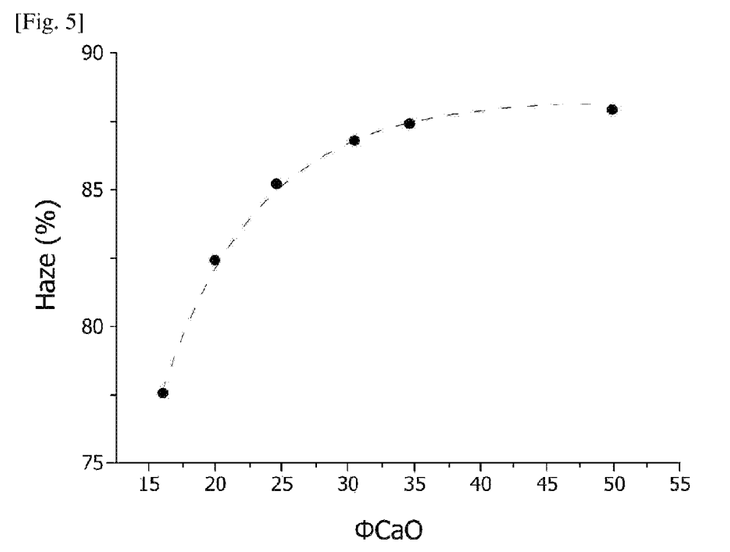
FIG. 5 is a graph showing a relation between a haze and a content of a moisture absorbent.

FIG. 5 is a graph showing a relation between a content of the moisture absorbent and the haze.

As shown in FIG. 5, a value of the haze gradually increases as the content of the moisture absorbent increases. Therefore, the content of the moisture absorbent may be a main factor for determining the value of the haze.

The encapsulant film of the present application may have various structures and may be made of, for example, a single layer, or multiple layers as described above. When the encapsulant film has a two-layer structure, each layer may have the same or different components.

The encapsulant film may further include, for example, a substrate. The substrate may be disposed in, for example, either or both surfaces of the film. The substrate may be, for example, a release-treated substrate. Substrates used in the related art may be used without limitation.

The encapsulant film may be applied to encapsulate and protect various objects. In particular, the film may be effective in protecting an object including an element that is sensitive to external factors, for example, water or moisture. Examples of the object to which the encapsulant film may be applied may include a photovoltaic device, a rectifier, a transmitter, an organic electronic device such as an organic light emitting diode (OLED) and the like; a solar cell; a rechargeable battery, and the like, but the object is not limited thereto.

The encapsulant film of the present application may be applied to encapsulate an electronic device. An electronic device including an upper substrate; a lower substrate; and an encapsulant film having a film encapsulating an element between the upper substrate and the lower substrate may be exemplified. In the above description, the term "element" may refer to any component of the electronic device. A representative example of the element that may be protected by the film may include an organic electronic element such as an organic light emitting element and the like, but the element is not limited thereto.

In an example, the film includes the above-described moisture absorbent, and may be an encapsulant film that is evaluated as having high reliability through a haze measurement.

In the electronic device, the upper substrate and the lower substrate may be disposed to face each other. Also, the element is formed in a surface of the lower substrate, and the surface of the lower substrate may be a surface facing the upper substrate. The film is placed between the upper and lower substrates, and the film may substantially cover an entire surface of the element. Also, when the film has a multi-layer structure, a layer containing less moisture absorbent may be attached closer to the element, as described above. Therefore, it is possible to provide an electronic device having excellent interfacial adhesion between the encapsulant film and the element or the lower substrate.

In an example, the electronic device may be the organic electronic device. The encapsulant film may exhibit an excellent water barrier property and optical property in the organic electronic device, and may efficiently fix and support the upper substrate and the lower substrate. Also, for example, when the moisture absorbent is manufactured in a nano-scale size and is uniformly dispersed in the resin, the encapsulant film may exhibit excellent transparency, and a stable encapsulant film may be formed regardless of a type of the organic electronic device such as a top emission or bottom emission.

The organic electronic device may have a general configuration known in the related art except that the encapsulant film is formed of the above-described film. For example, as the lower and/or upper substrate, glass, a metal, a polymer film, and the like, which are generally used in the related art, may be used. Also, the organic electronic element may include, for example, a pair of electrodes, and a layer of an organic material formed between the pair of electrodes. Here, either of the pair of electrodes may be formed as a transparent electrode. Also, the layer of the organic material may include, for example, a hole transport layer, a light emitting layer, and an electron transport layer.

In the above description, when the film is applied to the element, the film is laminated in contact with the element. For example, the film may be applied such that the film covers an entire surface of the element.

Also, lamination of the film in contact with the element may include, for example, a process in which the film comes in contact with the element, and the film is heated to have fluidity and is compressed onto the element. Therefore, even in an electronic device having a large area, it is possible to provide an electronic device that has no performance decrease due to bubbles and the like.

Also, in order to prevent bubbles and the like from being generated between the element and the film, the compression may be performed using a vacuum press and the like.

Also, after the film is laminated in contact with the element, the film may be cured. For example, a curing process may be performed in an appropriate heating chamber or ultraviolet chamber according to a curing method of the curable resin. Heating conditions or irradiating conditions of active energy rays may be appropriately selected in consideration of stability of the electronic device, curing property of the curable resin composition, and the like.

According to another embodiment of the present application, there is provided a method of evaluating reliability of an encapsulant film using the film. As described above, when the encapsulant film of the present application satisfies General Equations 1 and 2, according to such characteristics, it is possible to evaluate reliability of the film by measuring the haze of the encapsulant film including the moisture absorbent. When the organic electronic device panel is manufactured, since it is possible to determine availability of the film simply by measuring the haze before the encapsulant film is used, it is possible to provide the film capable of minimizing a failure rate of the organic electronic device.

In the related art, an encapsulation structure in which an organic light emitting element is covered by a glass can or a metal can having a getter or a moisture absorbent provided therein and is fixed with an adhesive has a problem in that air or oxygen is mixed in a gap formed when the organic light emitting element formed on the substrate and the glass can or the metal can having a getter or a moisture absorbent provided therein are separated, which may decrease a lifespan of the organic light emitting element. Therefore, an encapsulant adhesive film for directly covering and sealing the organic light emitting element is used. However, some encapsulant adhesive films have a good adhesive property but have a low heat resistant property and water barrier property. Accordingly, in order to solve such problems, an encapsulant film manufactured by dispersing a moisture absorbent such as a metal oxide having water reactivity in an adhesive film is used. In the encapsulant film containing the moisture absorbent, since the moisture absorbent chemically absorbs the water that has penetrated into the film, it is possible to decrease a rate of water penetration into the organic light emitting element.

Before the encapsulant film containing a water-reactive moisture absorbent as described above is applied to the panel in order to encapsulate the organic light emitting element, it is necessary to determine reliability. This is because, when some of the moisture absorbent in the encapsulant film has already reacted with water during a process of manufacture, transportation, storage, and the like of the encapsulant film, the individual number of the moisture absorbent which may block water when the film is applied to the panel decreases and thereby reliability of the encapsulant film decreases.

Before the film is applied to the panel, conventional methods of evaluating reliability of the water barrier property of the encapsulant film containing the moisture absorbent include a weight increase method, a calcium test method, and the like. The weight increase method is based on a principle that weight increases while the film reacts with water, but it is inaccurate since a content of a binder resin with respect to the moisture absorbent and a glass transition temperature are high. Another method, the calcium test method is based on a property in which calcium is oxidized by water and becomes transparent. In the calcium test method, calcium is deposited on glass, sealed by the encapsulant adhesive film and the glass, and remains under conditions of a relative humidity of 85% at 85° C. for a predetermined time. Then, a time at which calcium becomes transparent is used to evaluate reliability. However, this method consumes time for preparing a sample, and it takes 300 hours or more for water to penetrate into calcium in a test specimen. Therefore, this method is inappropriate as a reliability evaluation method of the encapsulant film immediately before the film is applied to the panel in a production stage.

Therefore, in order to introduce a simpler and more accurate evaluation method than the reliability evaluation method of the encapsulant film in the related art, the inventors devised an evaluation method using haze measurement.

As an example, in an evaluation method of the present application, haze of a film including a base resin and a moisture absorbent is measured within one hour from a time point at which the film is taken out of a water-resistant sealed envelope under conditions of a relative humidity of 50% at 25° C., and the measured haze value may be used to evaluate a reliable lifespan of the film. Also, in this case, the reliable lifespan of the film may be evaluated as being higher when the measured haze value of the film is higher.

Haze refers to turbidity (a degree of turbidity) caused by the moisture absorbent included in the film. The haze may be generally measured by a haze meter and represented by the following equation. The haze may be measured according to, for example, the ASTM D 1003 standard.

Haze value (%)=(diffuse transmittance($Td$)/total light transmittance ($Tt$))×100

In the above equation, the total light transmittance is a sum of a diffuse transmittance and a parallel transmittance. That is, the diffuse transmittance is obtained by subtracting the parallel transmittance from the total light transmittance.

Evaluating reliability of the water barrier property of the encapsulant film by measuring only the haze is an accurate evaluation method in terms of the following aspects.

First, it was determined that the film manufactured by dispersing fillers having the same size and content under the same conditions has a constant haze value. Therefore, when the encapsulant film being stored before application of the film is a product of the same grade including a moisture absorbent having the same size and content, the evaluation method of the present application may be applied to panel mass production.

Also, when the film is left in wet conditions, a decrease in the haze was determined. As described above, due to a hydration reaction of the moisture absorbent included in the encapsulant film with water that penetrates into the film, a hydrate, which is an aggregate of metal oxides, is generated from an outermost portion of the moisture absorbent, downsizing of an effective moisture absorbent that may react with water may be caused and thereby the haze decreases. Also, when a refractive index of the moisture absorbent is changed by the hydration reaction, the refractive index matches a refractive index of an organic binder and the haze decreases. Accordingly, in order to apply the encapsulant film being stored to the panel, it is necessary to secure the individual number of effective moisture absorbent which may react with water to a predetermined level or more, which means that the haze needs to be maintained to a predetermined level or more.

Finally, it was determined that there is a correlation between a decrease in the haze and a decrease in the water barrier property, that is, a lifespan of the encapsulant film. Films having the same grade and having the same moisture absorbent dispersed therein were left under the same conditions for a predetermined time, and the haze and the water penetration distance were simultaneously measured to determine the water barrier property. As a result, it was determined that the water penetration distance becomes greater in the test specimen as the haze decreases. Therefore, it may be understood that a correlation between a decrease in the haze and the lifespan of the film resulting from the water barrier property is established.

Therefore, unlike the conventional evaluation method, it is possible to evaluate reliability of the lifespan of the encapsulant film simply by measuring the haze. Since this method does not require a long time as in the calcium test method and has no influence from the binder resin or other components as in the weight increase method, it is an accurate evaluation method.

In an example, the haze value of the film measured by the above method may satisfy the following General Equation 4.

$$Hz = -me^{-\varphi hr(n_g/n-1)^2}$$ [General Equation 4]

In General Equation 4, Hz represents a haze value (%) of the film that is measured within one hour from a time point at which the film is taken out of the water-resistant sealed envelope under conditions of a relative humidity of 50% at 25° C. using the haze meter, m represents a value greater than 0, Φ represents a content of the moisture absorbent with respect to the base resin, h represents a thickness of the film, r represents an average particle diameter of the moisture absorbent, $n_g$ represents a refractive index of the moisture absorbent, and n represents a refractive index of the base resin.

As described above, the haze value of the film may be a value that is changed by the content of the moisture absorbent, the thickness of the film, the average particle diameter of the moisture absorbent, the refractive index of the moisture absorbent, and the refractive index of the base resin, which may satisfy the above relation. Therefore, in the method of the present application, it is possible to evaluate reliability according to an absolute value of the haze and evaluate reliability according to various haze values in consideration of the above parameters. For example, as described above, a haze of 10 is not unconditionally evaluated as having a shorter reliable lifespan than a haze of 20. Since evaluation may be performed in consideration of the parameters in General Equation 4, it is possible to evaluate the reliable lifespan more accurately.

Also, in the method of the present application, the measured haze value of the film may satisfy the following General Equation 1.

$$D = k/Hz \qquad \text{[General Equation 1]}$$

In General Equation 1, Hz represents a haze value (%) of the film that is measured within one hour from a time point at which the film is taken out of the water-resistant sealed envelope under conditions of a relative humidity of 50% at 25° C. using the haze meter, D represents a water penetration distance (mm) of the film that is measured after the film of which a haze is measured is laminated between two glass substrates and maintained under conditions of a temperature of 85° C. and a relative humidity of 85% for 0 to 1500 hours, and k represents a value equal to or greater than one as a proportionality constant.

In the evaluation method of the present application, the measured haze value of the film satisfies General Equation 1 and a relation between the measured haze value of the film and the water penetration distance may be inversely proportional. For example, as the haze value of the film increases, the water penetration distance of the film may decrease. That is, in the method of the present application, it is possible to evaluate the reliable lifespan of the film simply by measuring the haze using the fact that water does not easily penetrate into the film when a higher haze value of the film is measured.

The evaluation method may be performed by comparing haze values of two or more films. In this case, the evaluation method may be applied to the haze values measured from the encapsulant films including the moisture absorbent having the same size and type under the same conditions. For example, measurements of the water penetration distance of the two or more films may be performed after specimens are manufactured while the encapsulant films are interposed between glasses and left in a relative humidity of 85% at 85° C. for 0 to 1500 hours. In this case, it is preferred that a time at which the specimens are maintained in these conditions is the same time from 0 to 1500 hours.

Another embodiment of the present application relates to a device for measuring reliability of a film used in the evaluation method.

Figure 6:
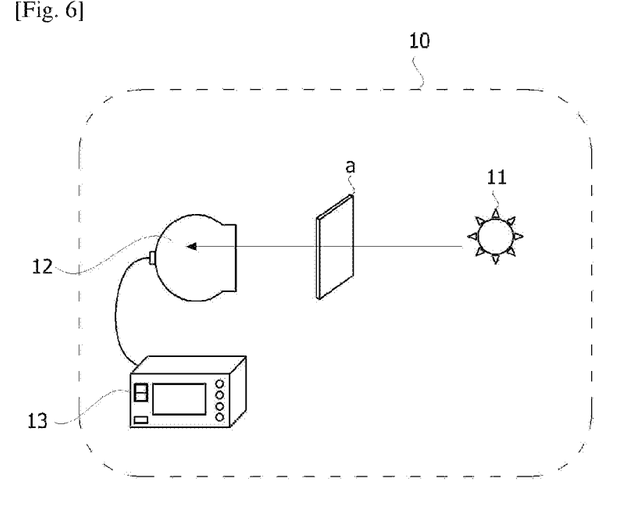
FIG. 6 is a diagram schematically illustrating an exemplary reliable lifespan measurement device of the present application.

FIG. 6 is a diagram schematically illustrating an exemplary measuring device.

As illustrated in FIG. 6, the reliability measuring device of the present application includes a light source 11, an integrating sphere 12, and a measuring unit 13.

The light source 11 is included in the measuring device of the present application in order to radiate light onto a sample film. The light source 11 radiates light necessary for measuring the haze of the sample film, and the light source 11 used in a general haze measuring device may be used for the measuring device of the present application.

The integrating sphere 12 is a member configured to detect light penetrating the sample film and measure the haze. The integrating sphere 12 is formed such that light passing through the sample film is incident, and the integrating sphere 12 used in the general haze measuring device may be used for the measuring device of the present application. The integrating sphere 12 measures the haze by detecting total transmitted light and scattered light of incident light by the sample film. In this case, the integrating sphere 12 may calculate the diffuse transmittance (Td) and the total light transmittance (Tt) by detecting diffused light and total transmitted light.

The measuring unit 13 is a member configured to measure reliability of the film using the haze value measured by the integrating sphere 12, for example, may be a calculating device having an algorithm that evaluates the reliable lifespan as being longer when the haze value is higher.

In an example, the measuring unit 13 may include an input unit configured to receive the haze value of the film measured by the integrating sphere 12, an evaluation unit configured to evaluate reliability of the film based on the received haze value, and a display unit configured to display the evaluation result.

For example, the haze value measured by the integrating sphere 12 may be input to the input unit through an electrical signal. Also, at least one selected from the group consisting of the content of the moisture absorbent in the sample film, the average particle diameter of the moisture absorbent, the refractive index of the moisture absorbent, the thickness of the sample film, and the refractive index of the base resin in the sample film may be additionally input to the input unit.

After the reliable lifespan is evaluated based on the input haze value and the additionally input values, the evaluation unit delivers the evaluation result to the display unit.

In an example, the evaluation unit may have an algorithm that evaluates the reliable lifespan as being higher when the haze value is higher.

For example, in order to evaluate reliability according to the absolute value of the haze, the evaluation unit may include a first algorithm in which the absolute value of the haze measured within one hour from a time point at which the sample film is taken out of the water-resistant sealed envelope under conditions of a relative humidity of 50% at 25° C. is graded and a grade of the lifespan is classified based thereon. When the evaluation unit evaluates the reliable lifespan of the film according to the first algorithm, the absolute value of the haze value of the sample film is simply used as a reference and the grade of the reliable lifespan may be evaluated based on the absolute value.

In another embodiment of the evaluation unit, the evaluation unit may include a second algorithm that may evaluate the absolute value of the haze in consideration of other parameters influencing the haze value, for example, the content of the moisture absorbent in the sample film, the average particle diameter of the moisture absorbent, the refractive index of the moisture absorbent, the thickness of the sample film or the refractive index of the base resin in the sample film, which are additionally input to the input unit. For example, in the second algorithm, m may be calculated by the following General Equation General Equation 4.

$$Hz = -me^{-\varphi hr(n_g/n-1)^2} \qquad \text{[General Equation 4]}$$

In General Equation 4, Hz represents a haze value (%) of the film that is measured within one hour from a time point at which the film is taken out of the water-resistant sealed envelope under conditions of a relative humidity of 50% at 25° C. using the haze meter, m represents a value greater than 0, Φ represents a content of the moisture absorbent with respect to the base resin, h represents a thickness of the film, r represents an average particle diameter of the moisture absorbent, $n_g$ represents a refractive index of the moisture absorbent, and n represents a refractive index of the base resin.

As described above, the haze value of the film may be a value that is changed by the content of the moisture absorbent, the thickness of the film, the average particle diameter of the moisture absorbent, the refractive index of the moisture absorbent, and the refractive index of the base resin, which may satisfy the above relation. Therefore, in the evaluation unit of the measuring device of the present application, reliability may be evaluated by the absolute value of the haze by the first algorithm, and reliability may be evaluated by various haze values in consideration of the parameters by the second algorithm. For example, as described above, a haze of 10 is not unconditionally evaluated as having a shorter reliable lifespan than a haze of 20. Since evaluation may be performed in consideration of the parameters in General Equation 4, it is possible to evaluate the reliable lifespan more accurately.

The display unit may display a display result received from the evaluation unit and may use, for example, various display devices known in the art.

Advantageous Effects

The present application may provide a film that may be provided for an evaluation method in which reliability of an encapsulant film is simply and easily evaluated only by measuring a haze immediately before the encapsulant film is used, thereby a failure of a product is determined and reliability may be predicted.

MODES OF THE INVENTION

Hereinafter, while the present application will be described in detail with reference to Examples and Comparative Examples, the scope of the present application is not limited to the following Examples.

Example 1—Manufacturing of Pressure-Sensitive Adhesive Film (1) Preparation of a Solution for Forming an Encapsulant Film 100 g of calcined dolomite having an average particle diameter of 5 μm was input as a moisture absorbent, MEK having a solid concentration of 50 wt % was input as a solvent, and a ball milling operation was performed to prepare a moisture absorbent solution. 200 g of a silane-modified epoxy resin (KSR-177, Kukdo Chemical Co., Ltd.) and 150 g of a phenoxy resin (YP-50, Dong Do Tech Co., Ltd.) were input in a reactor at room temperature and diluted with methylethylketone. 4 g of imidazole (Shikoku Chemicals Corp.) serving as a curing agent was input to the homogenized solution and then high-speed stirring was performed for one hour to prepare a water barrier layer solution. The moisture absorbent solution prepared in advance was input to the solution such that a content of the calcined dolomite was 10 parts by weight with respect to 100 parts by weight of a base resin of the encapsulant film, and mixed to prepare an encapsulant film-forming solution. In this case, a refractive index of the used epoxy-based base resin after curing was 1.52 and a refractive index of the calcined dolomite was 1.8, which were measured by an Abbe refractometer. Due to a hydration reaction when the calcined dolomite was reacting with water, the refractive index changed to 1.57 and became similar to the refractive index of the base resin.

(2) Manufacturing of Film

The –solution for forming an encapsulant film prepared as above was applied onto a release surface of a release PET and dried for 10 minutes at 110° C. An encapsulant film having a thickness of 40 μm was formed, and then was placed and stored in a water-resistant sealed envelope such that it was not exposed to conditions of a relative humidity of 50% at 25° C.

Example 2

An encapsulant film was manufactured by the same method as in Example 1 except that the moisture absorbent was input to have a content of 20 parts by weight with respect to 100 parts by weight of the base resin.

Example 3

An encapsulant film was manufactured by the same method as in Example 1 except that the moisture absorbent was input to have a content of 30 parts by weight with respect to 100 parts by weight of the base resin.

Example 4

An encapsulant film was manufactured by the same method as in Example 1 except that the moisture absorbent was input to have a content of 50 parts by weigh with respect to 100 parts by weight of the base resin.

Example 5

An encapsulant film was manufactured by the same method as in Example 2 except that a moisture absorbent having an average particle diameter of 100 nm was input.

Example 6

An encapsulant film was manufactured by the same method as in Example 1 except that the manufactured film was exposed to conditions of a relative humidity of 50% at 25° C. for 3 hours and then was placed and stored in a water resistant sealed film.

Example 7

An encapsulant film was manufactured by the same method as in Example 1 except that the manufactured film was exposed to conditions of a relative humidity of 50% at 25° C. for 5 hours and then was placed and stored in a water resistant sealed film.

Comparative Example 1

An encapsulant film was manufactured by the same method as in Example 1 except that the manufactured film was exposed to conditions of a relative humidity of 50% at 25° C. for 10 hours and then was placed and stored in a water resistant sealed film.

Comparative Example 2

An encapsulant film was manufactured by the same method as in Example 1 except that the moisture absorbent was input to have a content of 5 parts by weight with respect to 100 parts by weight of the base resin.

Comparative Example 3

An encapsulant film was manufactured by the same method as in Example 1 except that a moisture absorbent having an average particle diameter of 100 nm was input.

In Examples and Comparative Examples, physical properties were evaluated by the following methods, and Tables 1 and 2 show results thereof.

1. Measurement of Viscosity

While a temperature was increased from 25° C. to 130° C., viscosity of the films manufactured in Examples was measured using an advanced rheometric expansion system (ARES) under conditions of a frequency of 1 Hz and a strain of 5%.

2. Measurement of Haze

In order to measure a haze of the films manufactured in Examples and Comparative Examples, separate specimens was prepared. Since the haze changes depending on a thickness, all specimen films were manufactured to have the same thickness of 40 μm and evaluation was performed. In a curable product, when a curing agent is dispersed in the form of a powder, light is scattered due to the curing agent. In order to remove such an influence, an adhesive film was cured on a release film, the curing agent was entirely melted, and then a haze having only an influence of the moisture absorbent was measured. On the other hand, when a non-curable film was used, the haze was directly evaluated. As a haze meter, NDH-5000 (Nippon Denshoku Industries Co., Ltd.) was used for a measurement, and a measurement specification was JIS K7105. A haze value was measured after an exposure time had elapsed under conditions of a relative humidity of 50% at 25° C. of the following Table 1 from a time point at which the manufactured specimen was taken out of a water-resistant sealed envelope.

Meanwhile, the haze values of the specimens of Examples 1 to 7 and Comparative Examples 1 to 3 were measured while changing a content and a particle diameter of the moisture absorbent and maintaining exposure conditions of a relative humidity of 50% at 25° C. Table 1 shows the results. In order to compare haze values when the moisture absorbent having the same particle diameter and the same content is included, four separate specimens were manufactured in addition to those of Examples 1 to 7 and Comparative Examples 1 to 3, and the haze values of the specimens were measured by the above method. Table 2 shows the results.

3. Determination of Damage of Organic Electronic Device

An organic light-emitting panel having a bezel of 6 mm was manufactured using the adhesive film in Examples 1 to 7 and Comparative Examples 1 to 3 and left in a constant temperature and humidity chamber under conditions of a temperature of 85° C. and a relative humidity of 85% for 1000 hours, and then occurrence of dark spots was observed using an optical microscope. Table 1 shows the results.

4. Measurement of Water Penetration Distance

The film having a thickness of 40 μm manufactured in Example was cut to a size of 40 mm×40 mm, placed at a center between two plate glasses having sizes of 1 mm×50 mm×50 mm, vacuum thermo-compressed, and, when it was a curable adhesive film, cured. The manufactured adhesive film was maintained under conditions of a temperature of 85° C. and a relative humidity of 85% for 0 hours to 1200 hours, and a length to which water penetrated from an outermost edge of the adhesive film toward a center of the film and transparency occurred was measured using an optical microscope.

Meanwhile, the water penetration distances of the specimens of Examples 1 to 7 and Comparative Examples 1 to 3 were measured while changing a content and a particle diameter of the moisture absorbent. Table 1 shows the results. Four separate specimens including the moisture absorbent having the same particle diameter and the same content were manufactured and exposed to conditions of a relative humidity of 50% at 25° C. for 0 hours, 3 hours, 6 hours, and 16 hours, respectively. Then, when 73 hours, 242 hours, 315 hours, 404 hours, 574 hours, 759 hours, 877 hours, 978 hours, and 1118 hours had elapsed under conditions of a temperature of 85° C. and a relative humidity of 85%, the water penetration distances of the specimens were measured by the above method.

TABLE 1

| | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Content of moisture absorbent (wt %) | 10 | 20 | 30 | 50 | 20 | 10 | 10 | 10 | 5 | 10 |
| Average particle diameter of moisture absorbent | 5 μm | 5 μm | 5 μm | 5 μm | 100 nm | 5 μm | 5 μm | 5 μm | 5 μm | 100 nm |
| Exposure time of film (relative humidity of 50% at 25° C.) | 0 | 0 | 0 | 0 | 0 | 3 | 5 | 10 | 0 | 0 |
| Haze (%) | 50 | 70 | 80 | 88 | 30 | 47 | 43 | 29 | 25 | 20 |
| Viscosity (pa · s) | $1.6 \times 10^8$ | $1.2 \times 10^8$ | $0.9 \times 10^8$ | $0.7 \times 10^8$ | $2.3 \times 10^8$ | $1.6 \times 10^8$ | $1.6 \times 10^8$ | $1.6 \times 10^8$ | $1.1 \times 10^8$ | $1.7 \times 10^8$ |

TABLE 1-continued

|  | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Occurrence of dark spots | x | x | x | x | x | x | x | ○ | ○ | ○ |
| Water penetration distance (mm) after being left at 85° C. and RH of 85% for 300 hrs | 4 | 3.4 | 2.8 | 2.1 | 2.5 | 4.2 | 4.5 | 5 | 6.2 | Immeasurable |

TABLE 2

| Haze | Exposure time (hr) in conditions of relative humidity of 50% at room temperature | Elapsed time under conditions of temperature of 85° C. and relative humidity of 85% (hr) | | | | | | | | |
|---|---|---|---|---|---|---|---|---|---|---|
| | | 73 | 242 | 315 | 404 | 574 | 759 | 877 | 978 | 1118 |
| | | Water penetration distance (mm) | | | | | | | | |
| 75.8 | 0 | 1.39 | 2.54 | 2.92 | 3.28 | 3.95 | 4.69 | 4.95 | 5.23 | 5.68 |
| 73.8 | 3 | 1.43 | 2.69 | 3.10 | 3.49 | 4.11 | 4.89 | 5.19 | 5.48 | 5.89 |
| 69.1 | 6 | 1.59 | 2.92 | 3.33 | 3.75 | 4.51 | 5.28 | 5.64 | 6.06 | 6.5 |
| 45.2 | 16 | 2.5 | 4.8 | 5.40 | 6.30 | 7.60 | 8.70 | 9.40 | 10.1 | 10.9 |

As shown in Table 1, it can be seen that the haze value of the encapsulant film may variously change according to parameters such as a content, an average particle diameter, etc. of the moisture absorbent. When the same moisture absorbent is used, if the haze value increases, the water penetration distance decreases and no dark spots occur. Accordingly, it may be determined that the organic electronic device has no damage. Also, as in Example 1 and Comparative Example 1, even when the film including the moisture absorbent having the same particle diameter and content is used, water does not pass through a bezel of 6 mm in a film having a high haze value. Accordingly, a relation between the water penetration distance and the haze can be confirmed.

Meanwhile, as can be seen from the result of Table 2, in the encapsulant film having the same moisture absorbent, it may be seen that the haze value decreases as the exposure time in conditions of a relative humidity of 50% at 25° C. increases before the film is applied to the panel, and the water barrier property decreases as the haze value decreases.

REFERENCE NUMERALS

10: measurement device
11: light source
12: integrating sphere
13: evaluation unit
a: sample film

The invention claimed is:

1. An encapsulant film comprising a base resin and a moisture absorbent, and satisfying General Equation 1 to General Equation 3:

$$D = k/Hz \quad \text{[General Equation 1]}$$

$$D = -\alpha \times Hz + \beta \quad \text{[General Equation 2]}$$

$$Hz \geq 30\% \quad \text{[General Equation 3]}$$

wherein Hz represents a haze value (%) of the film that is measured using a haze meter within one hour from a time point at which the film is taken out of a water-resistant sealed envelope under conditions of a relative humidity of 50% at 25° C., D represents a water penetration distance (mm) of the film that is measured after the film of which a haze is measured is laminated between two glass substrates and maintained under conditions of a temperature of 85° C. and a relative humidity of 85% for 0 to 1500 hours, and k is a value equal to or greater than one, wherein $\alpha$ is 0.01 or more, and $\beta$ is 1.0 or more and is greater than D, wherein the moisture absorbent is included in an amount of 20 to 200 parts by weight with respect to 100 parts by weight of the base resin, wherein the haze value of the film decreases due to a change in a refractive index of the moisture absorbent caused by the hydration reaction of the moisture absorbent with water, wherein the film is a multi-layer film comprising a first layer which contacts with an organic electronic element and a second layer that does not contact with the organic electronic element, and wherein the first layer includes 0 to 20% of the moisture absorbent and the second layer includes 80 to 100% of the moisture absorbent with respect to a mass of the total moisture absorbent in the film.

2. The encapsulant film of claim 1, wherein the film is in a solid or semi-solid state at room temperature.

3. The encapsulant film of claim 1, wherein the film has a viscosity of $10^6$ poise or more at room temperature.

4. The encapsulant film of claim 1, wherein a water vapor transmission rate of a film having a thickness of 100 μm measured in a relative humidity of 100% at 100° C. in a thickness direction of the film is 50 g/m²·day or less.

5. The encapsulant film of claim 1, wherein the base resin is a styrene-based resin, a polyolefin-based resin, a polyoxyalkylene-based resin, a polyester-based resin, a polyvinylchloride-based resin, a polycarbonate-based resin, a polyphenylene-sulfide-based resin, mixtures of hydrocarbons, a polyamide-based resin, an acrylate-based resin, an epoxy-based resin, a silicone-based resin, a fluorine-based resin, or mixtures thereof.

6. The encapsulant film of claim 5, wherein the base resin is a copolymer of olefin-based compounds having a carbon-carbon double bond.

7. The encapsulant film of claim 5, wherein the base resin is the epoxy-based resin.

8. The encapsulant film of claim 7, wherein the epoxy-based resin includes a cyclic structure in its molecular structure.

9. The encapsulant film of claim 7, wherein the epoxy-based resin is a silane-modified epoxy resin.

10. The encapsulant film of claim 5, wherein the first layer and the second layer include either of the polyolefin-based resin or the epoxy-based resin.

11. The encapsulant film of claim 1, wherein the moisture absorbent is a water reactive adsorbent, a physical adsorbent, or mixtures thereof.

12. The encapsulant film of claim 11, wherein the water reactive adsorbent is alumina, a metal oxide, a metal salt, or phosphorus pentoxide, and the physical adsorbent is silica, zeolite, titania, zirconia, or montmorillonite.

13. The encapsulant film of claim 11, wherein the water reactive adsorbent is at least one selected from the group consisting of $P_2O_5$, $Li_2O$, $Na_2O$, $BaO$, $CaO$, $MgO$, $Li_2SO_4$, $Na_2SO_4$, $CaSO_4$, $MgSO_4$, $CoSO_4$, $Ga_2(SO_4)_3$, $Ti(SO_4)_2$, $NiSO_4$, $CaCl_2$, $MgCl_2$, $SrCl_2$, $YCl_3$, $CuCl_2$, $CsF$, $TaF_5$, $NbF_5$, $LiBr$, $CaBr_2$, $CeBr_3$, $SeBr_4$, $VBr_3$, $MgBr_2$, $BaI_2$, $MgI_2$, $Ba(ClO_4)_2$, and $Mg(ClO_4)_2$.

14. The encapsulant film of claim 1, wherein the film satisfies General Equation 4:

$$Hz = -me^{-\varphi hr(n_g/n-1)^2} \quad \text{[General Equation 4]}$$

where, in General Equation 4,

Hz is the same as defined in claim 1, m represents a value greater than 0,

Φ represents a content of the moisture absorbent with respect to the base resin, h represents a thickness of the film, r represents an average particle diameter of the moisture absorbent, $n_g$ represents a refractive index of the moisture absorbent, and n represents a refractive index of the base resin.

15. An organic electronic device, comprising, a substrate;

an organic electronic element formed on the substrate; and an encapsulant film encapsulating the organic electronic element according to claim 1, wherein the film adheres to an entire surface of the organic electronic element.

* * * * *